United States Patent [19]

Doutre et al.

[11] Patent Number: 4,555,662
[45] Date of Patent: Nov. 26, 1985

[54] METHOD AND APPARATUS FOR THE DETECTION AND MEASUREMENT OF PARTICULATES IN MOLTEN METAL

[75] Inventors: Don A. Doutre, Jonquiere; Roderick I. L. Guthrie, Westmount, both of Canada

[73] Assignee: Limca Research Inc., Montreal, Canada

[21] Appl. No.: 471,908

[22] Filed: Mar. 3, 1983

[51] Int. Cl.⁴ ............................................. G01N 27/00
[52] U.S. Cl. ..................................... 324/71.4; 164/4.1; 266/99; 377/12
[58] Field of Search .......................... 324/71.1, 71.4; 377/10–12; 164/4.1, 150; 266/78, 80, 99

[56] References Cited

U.S. PATENT DOCUMENTS

3,259,842  7/1966  Coulter et al. .................... 377/12
3,921,006  11/1975  Pontigny ........................... 324/71.4
3,963,984  6/1976  Coulter ............................. 324/71.1

Primary Examiner—Ernest F. Karlsen
Assistant Examiner—Kevin D. O'Shea
Attorney, Agent, or Firm—Hirons, Rogers & Scott

[57] ABSTRACT

The invention provides a new method and apparatus for the detection of non-conductive particulates in molten metals, such as aluminum, gallium, zinc and lead, that can be liquified and drawn into a suitable refractory container. The passage into the container is of very small diameter (about 300 micrometers for aluminum) and it forms part of a current path between two electrodes carrying a current of about 1 to 500 amperes. The path is surrounded by liquid metal which forms an effective Faraday cage screening the path, enabling the passage of a particulate of about 15 micrometers or larger to produce a voltage pulse between the electrodes of greater than 5 microvolts, which is detectable above the inevitable background noise, which is of about that value. The size of the pulse gives an indication of the particle size and appropriate measurement and sampling electronically of the pulses gives a rapid evaluation (less than 3 minutes) of the particle size distribution, giving the operator an opportunity of deciding immediately whether or not further cleansing of the metal is required.

9 Claims, 10 Drawing Figures

METHOD AND APPARATUS FOR THE DETECTION AND MEASUREMENT OF PARTICULATES IN MOLTEN METAL

FIELD OF THE INVENTION

The present invention is concerned with a new method and apparatus for the detection and measurement of the size of particulates in molten metal, and especially but not exclusively, to their detection and measurement in molten aluminum.

REVIEW OF THE PRIOR ART AND BACKGROUND OF THE INVENTION

Molten metals, particularly molten aluminum and steel, are frequently contaminated to some extent by entrained non-metallic inclusions that give rise to a variety of shortcomings or defects in the resulting finished products. Such inclusions can arise from a number of sources, for example, in aluminum through the entrainment of surface oxide films, from the formation of insoluble impurities such as coarse or clustered boride particles, or fine or coarse carbides and nitrides, from the oxidation of alloying elements such as magnesium, and from the erosion of the refractory linings of vessels used to hold or transport the liquid metal.

Problems that are caused by the presence of inclusions include the tearing of the metal during mechanical working operations, the presence of pin-holes and streaks in foils, surface defects and blisters in anodized sheet, and increased rates of breakage during the production of wire. These problems are becoming more acute as customers demand thinner, lighter products and better surface appearance, and as the proportion of recycled metal that is used in the production of some sheet metal products rises, with attendant increases in inclusion formation during remelting.

A variety of methods are currently available for removing inclusions from molten metals such as aluminum, and aluminum alloys including decantation, fluxing with reactive solid or gaseous mixtures (which may be combined with stirring), filtration, vacuum refining, and combinations thereof. It is also found helpful in the cleaning of liquid steel to produce turbulence in the melt, since this produces particle agglomeration and subsequent floating out of the agglomerate. The aim of these processes is to reduce the size and/or concentration of suspended inclusions to acceptably low levels. Each of these operations inevitably adds to the producer's costs.

In order to evaluate the effectiveness of these methods, producers have at their disposal a number of procedures for the evaluation of metal quality. Included in these are filtration rate tests, the metallographic examination of polished metal sections (either directly or following a preconcentration step such as filtration or centrifuging), non-destructive testing techniques such as ultra-sonic or eddy-current testing, counting the rate of defects appearing in sheet or foil, or counting the number of breakages per unit length of wire produced. Filtration rate tests can provide information relatively rapidly, but are unable to provide size distribution data. Since all the other procedures listed above entail a substantial time delay before the results are available the metal will usually be cast and possibly fabricated before the test results become available. In these circumstances the only course available to the producer when substandard metal quality is encountered is to downgrade the material, and perhaps to scrap the production lot.

Ideally, for control of commercial processes test results of liquid metal quality are needed within minutes. Additionally, the tests should provide information about the size and the concentration of any entrained inclusions. To this end the Reynolds Metal Co. has described in the Journal of Metals for October 1982 an ultrasonic, pulse-echo technique for detecting discontinuities in a sample of molten aluminum caused by unwanted inclusions. Such a system is said to be able to provide a rapid indication of the state of cleanliness of the liquid metal, but its ability to provide quantitative measurements of either the absolute concentration or the size distribution of inclusions has not as yet been demonstrated.

An apparatus for electrical zone sensing of suspended particles in a liquid is disclosed in U.S. Pat. No. 2,656,508 issued Oct. 20, 1953 to Wallace A. Coulter. In a typical apparatus a tube having an aperture in its wall is positioned within a larger vessel. A liquid electrolyte suspension containing the particles to be detected is placed in the vessel and is induced to flow through the aperture by establishing a fluid pressure differential between the interiors of the vessel and the tube. The vessel and the tube are both fabricated of an insulator, e.g. glass, and a constant electric current is placed across the aperture. The presence of a particle in the liquid flow through the aperture causes a change in the electrical resistance detected at the aperture and the electric voltage producing the constant current will vary directly with the resistance change each time a particle passes through the aperture. A detecting circuit determines the size of the passing particles from the change in resistivity caused by each particle, this depending upon the volume of electrolyte at the aperture displaced by the particle and by the resistivity of the kind of particles being sized. This information is amplified and processed by suitable electronic circuits.

This electrical sensing zone apparatus for particle size analysis is widely used in biology, haematology, geology, mineral processing and in many industries dealing with powders. All of the applications of the electrical sensing zone apparatus described above are carried out at moderate temperature using a suspending medium consisting of aqueous or organic electrolytic solutions.

DEFINITION OF THE INVENTION

It is therefore an object of the present invention to provide a new method and apparatus for the detection and measurement of the concentration and size distribution of suspended particulates in molten metal that is operative relatively rapidly.

It is another object to provide such a method that is operative relatively rapidly and can be employed during a processing operation on the molten metal.

In accordance with the present invention there is provided a method for the detection and measurement in a molten metal sample of suspended particulates of greater than a predetermined size whose electrical conductivities differ from that of the suspending molten metal including the steps of:

establishing a current path which will include the molten metal of the sample between two electrodes and through a passage of predetermined cross-sectional area, passing the molten metal sample in the current path and through the said passage while an electric current is maintained through the current path, and measuring the voltage drop between the said electrodes and detecting changes therein caused by the passage through the passage of said particulates.

Preferably, the said method includes the step of counting the number of said changes in voltage drop as a representation of the number of the said particulates in the sample, and measuring the size of the changes as representative of the sizes of the particulates causing the changes.

Also in accordance with the invention there is provided apparatus for the detection and measurement in a molten metal sample of suspended particulates of greater than a predetermined size whose electrical conductivities differ from that of the suspending molten metal medium comprising:

electrically insulating wall means providing a passage of predetermined size therethrough, a pair of electrodes disposed on opposite sides of the wall means to establish a current path between them through the molten metal of the sample and passing through the said passage, means for passing a sample of molten metal through the passage, means for passing an electric current between the two electrodes through the molten metal in the said current path at least while the molten metal sample is passing through the passage, and means connected to the two electrodes for detecting a change of voltage in the path resulting from the passage through the passage of the said particulates.

Preferably the said apparatus includes means for counting the number of said changes as representative of the number of said particulates, and for measuring the sizes of the changes as representative of the size of the particulates causing the changes.

DESCRIPTION OF THE DRAWINGS

Methods and apparatus which are particular preferred embodiments of the invention will now be described, by way of example, with reference to the accompanying diagrammatic drawings wherein.

DESCRIPTION OF THE PREFERRED EMBODIMENTS

Figure 1:
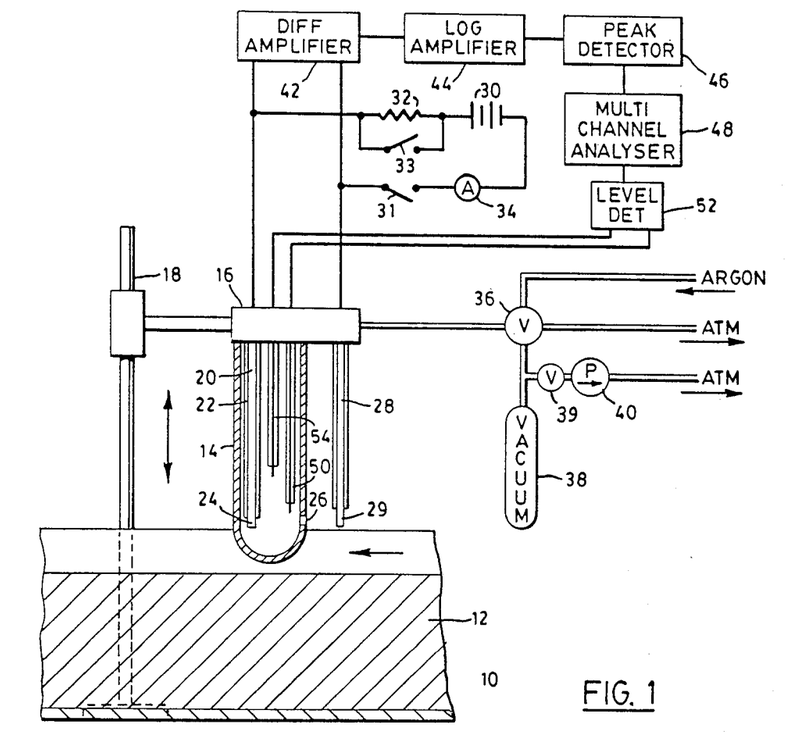
FIG. 1 is a schematic representation of apparatus of the invention.

The apparatus of the invention is illustrated schematically in FIG. 1 and its actual implementation in practice will be described as required. A trough 10 conveys the molten metal 12 to be tested from the furnaces in which it has been melted to subsequent treatment stages such as a degasser, filter bed and caster. Alternatively for an off-line test which is not illustrated, a sample of about 2 Kg of the metal would be transferred as quickly as possible from a holding furnace or transfer trough to a stirred test vessel heated as required to maintain the metal in molten condition.

In accordance with the invention, the cleanliness of the molten metal, either in the flowing stream or in the stationary test vessel, can then be examined by drawing a sample, by means of reduced pressure, into a sample-receiving test container or vessel 14 which is removably mounted by any suitable means in an end cap 16. The end cap is mounted by a standard 18 for vertical up and down movement, so that the test vessel 14 can be dipped at will into the flowing stream 12 and withdrawn therefrom. The end cap has four electrodes protruding downwardly therefrom, three of which are inside the container. The first of these three electrodes is a current-carrying electrode 20 consisting of a metal rod the upper part of which is encased in an insulating material 22, so that only the exposed lower tip 24 immediately adjacent to a passage 26 in the container wall is in electrical contact with molten metal that enters the container. A similar current-carrying electrode 28 is mounted by the end cap so as to extend outside the container parallel to the first electrode 20 with its bare lower tip also immediately adjacent to the passage 26. The resultant current path between the electrodes 20 and 28 and through the passage 26 is supplied with current from a battery 30 via a ballast resistor 32 that can be shunted when required by a switch 33, one of the leads including a switch 31 and an ammeter 34.

The end cap 16 also provides a fluid connection from the interior of the test container to a three-way valve 36, which permits the interior to be connected alternatively to a source of reduced pressure, or to a source of a suitable shielding inert gas, such as argon, or to the atmosphere. The reduced pressure source consists of a reservoir 38 which is exhausted as required in between tests through valve 39 by a pump 40. The pump is shut off while the tests are underway, so that any electrical noise produced by its electric motor does not hinder electrical signal processing, and so that any pulsations in flow of the evacuating gas are not transmitted to the entering molten metal. The two electrodes 20 and 28 are connected to a differential amplifier 42 and thence to a logarithmic amplifier 44, a peak detector 46 and multichannel analyser 48, which can also serve as a recorder. The analyser/recorder 48 is operated automatically so as to be switched on when sufficient metal has entered the container to contact the lower level electrode 50 of a metal level detector 52, and to be switched off when sufficient metal has entered the sample-receiving vessel to contact the upper level detection electrode 54 of the level detector.

Alternatively the analyser recorder can be operated manually, the sampling period used then being a fixed period of time as set by the operator.

Before use the interior of the container 14 is flushed with argon gas to avoid as much as possible contamination of the metal by air. The container is then lowered into the stream, and the valve 36 is operated to connect the container interior to the reduced pressure reservoir, whereupon the molten metal is drawn smoothly and rapidly through the passage 26. As soon as enough metal has entered the container to touch the tip 24 of the electrode 20 a current path is established between the two electrodes 20 and 28 and through the passage.

Figure 5:
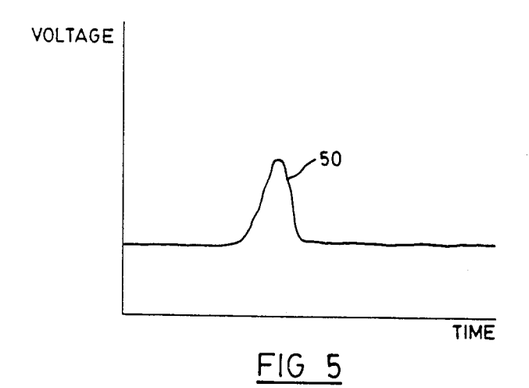
FIG. 5 is a representation of a record obtained with the apparatus of FIG. 1 illustrating the electrical pulse detected with an individual particle passing through the sensing zone of the apparatus.

The current flow is principally controlled by the ballast resistor 32 and this remains sufficiently constant (less than 1% variation) during signal processing. Since the area of contact between the liquid metal 12 and the electrodes 20 and 28 is limited to the tips 24 and 29, the only changes in voltage that are measured are those arising from the displacement of conducting fluid by particles passing through the passage 26. Each of these particles when sensed produces a record as illustrated by FIG. 5, consisting of a positive voltage pulse 50 over and above the steady state value.

Thus, as each particle passes through the passage 26 it displaces its own volume of the liquid metal and causes a change in the electrical resistance between electrodes 20 and 28. In the presence of an applied current, this resistance change causes the above-described transient voltage pulse to appear between the two electrodes 20 and 28. The magnitude of the transient voltage pulse is related to the equivalent spherical diameter of the particle according to the following equation as given by R. W. DeBlois and C. P. Bean in Review of Scientific Instruments (1970) 41,909:

$$\Delta V \simeq \frac{4 \rho \, I d^3}{\pi D^4} \qquad (1)$$

Where $\Delta V$ is the voltage change, $\rho$ is the electrical resistivity of the molten metal, I is the current, d is the equivalent spoherical particle diameter and D is the passage diameter.

Figure 6:
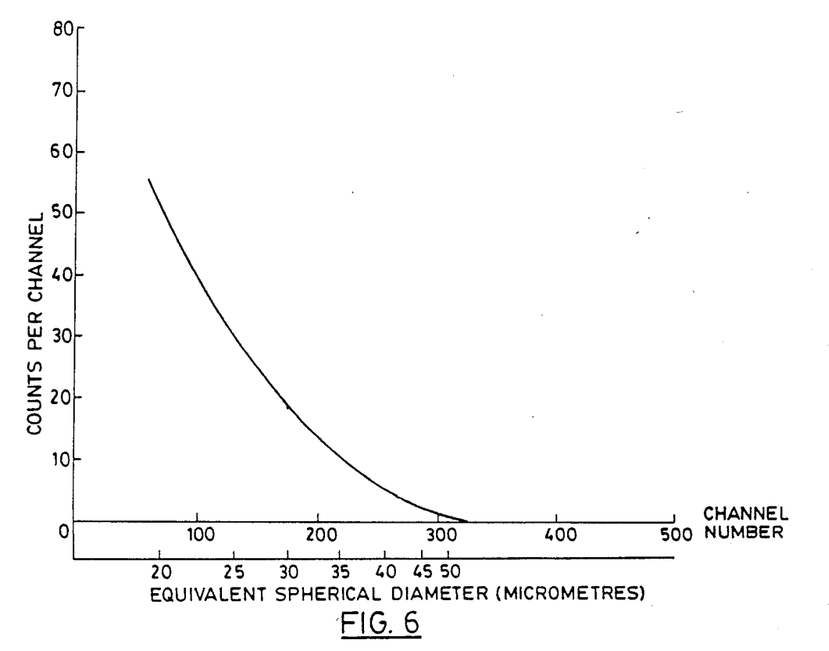
FIG. 6 is a representation of a composite record obtained with the apparatus of FIG. 1, showing a typical particle size distribution for a tested aluminum sample.

The voltage pulses that result from the passage of the particles are of relatively low amplitude superimposed on a large D.C. signal; these are fed to the differential pre-amplifier 42 and filtered to remove the large D.C. component and inevitable high frequency noise. The logarithmic amplifier 44 extends the dynamic range of the signal, and its output is fed to the peak detector which samples the signal and produces discrete pulses of fixed length that can be handled by the analyser 48. The analyser counts the number of these pulses and also analyses them as to size. The output of the analyser is therefore a histogram of particle number from which the particle concentration in the specimen can be determined, and also particle size distribution, as illustrated by FIG. 6. The analyser can include a cathode ray tube for immediate display of this histogram, or a recorder, or a memory store from which the information is obtainable at any time.

By adjustment of the gain of the amplifiers 42 and 44 and the current and knowing the input range of the multichannel analyser 48, it is thus possible by application of the above equation to relate each channel of the analyser 48 to an equivalent spherical diameter of a particle, so that passage through the passage of such a particle causes a count to appear in that channel. The y-axis of the graph of FIG. 6 is therefore representative of counts per channel, while the x-axis has the dual representation of the channel number of the analyser and the spherical diameter in micrometers equivalent to each channel.

Severe problems are involved in obtaining usable information as to particle count and size distribution of unwanted particulates when the liquid involved is a molten metal, and do not appear to have been overcome hitherto, but are overcome by the method and apparatus of the invention. In a specific apparatus that has been tested successfully the metal involved was aluminum at a temperature of about 700° C. (1260° F.). Other metals which have also been analysed with this apparatus are zinc at 450° C., lead at 400° C.,and gallium at 35° C.

Figure 4:
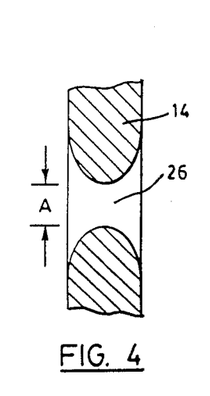

The sample-receiving container 14 that was employed is a tube of borosilicate glass (KIMBLE 45052) of length 20.0 cm, diameter 2.5 cm, and wall thickness 0.13 cm, while the orifice 18 is as illustrated by FIG. 4 of about 300 micrometers minimum diameter that has been formed by a flame-piercing procedure described below. The electrodes 20 and 28 are of steel rod of 6.5 mm diameter enclosed in a glass sheath of 1.0 mm thickness, with approximately 5.0 mm of the rod end exposed to the molten metal. Copper wire is unsatisfactory for this purpose, although other metals more resistant to attack by molten aluminum, such as titanium, or steel clad copper rods would also be adequate.

The volume of a typical sample between the level electrodes 50 and 54 is about 16 ml and takes about 60 seconds to draw into the vessel using a vacuum of about 12.5 cm (5 ins.) mercury. When the test container is immersed in a flowing stream such a sample will have been taken from about 300–600 kg of metal that has passed by the container. The molten metal can be blown out of the tube by use of the pressurized argon and the particle sizes again monitored. The apparatus is then immediately ready for a new test; alternatively the interior can be connected to atmosphere until the vacuum is relieved and then the tube replaced with a new one. It will be noted that the signal processing procedure could be reversed by applying positive pressure to the interior of a filled sample-receiving vessel and monitoring for the presence and size of the particulates as they are expelled through the passage and out into the surrounding melt; such a procedure can then be "backed-up" by applying suction to the vessel interior to draw liquid metal into it while monitoring the signal produced.

If a positive pressure source is used then preferably it is a quiescent source such as a pre-pumped reservoir of compressed gas so as to avoid the presence of pump pulsations during the test.

It is believed to be surprising that a molten metal can be handled in this manner, particularly molten aluminum, which is known to be chemically highly aggressive, and also to have a high surface energy so that considerable difficulty would be anticipated in attempting to pass it through an aperture of the necessary small size within a sufficiently short period of time and without freezing or any mechanical difficulty, such as enlargement of the passage by the flow of the molten metal through it. The passage diameter for the above-described preferred embodiment is about 300 micrometers, but a range of diameters can be used depending upon the metal under test and the size and nature of the particles to be examined. The diameter will in practice be in the range from 100 to 5000 micrometers, more usually from about 200 to about 500 micrometers. For example, the deleterious inclusions commonly found in aluminum are within the range of about 20–80 micrometers effective diameter. However, in the case of molten steel it is found to contain deoxidation products of size in the range about 10–80 micrometers, reoxidation products of size in the range about 100–500 micrometers, and slag particles of as yet unknown size, but many of which are believed to be of size about 1000 micrometers.

It is known that with a molten metal the conductivity is completely an electronic phenomenon, as contrasted with the ionic conductivity characteristic of the prior art Coulter apparatus employing an aqueous media described above. The currents that are required to obtain a useful reading can be very large and the battery 30 must be capable of delivering a steady current of about 1 to 500 amperes during the period of the test, depending upon the diameter of the orifice, the resistivity of the metal being tested and the sensitivity desired. In the case of molten aluminum, with an aperture diameter of 200 to 500 micrometers, a preferred narrower range of current is from 1 to 100 amperes corresponding to a current density through a 300 micrometer diameter aperture of from $1.4 \times 10^7$ to $1.4 \times 10^9$ amps/m$^2$ and a power density in a 300 micrometer diameter aperture of from $5 \times 10^7$ to $5 \times 10^{11}$ watts/meter$^3$. Despite these extraordinarily high power densities, the metal in the aperture does not vaporize during the test because of its short residence time in the passage.

Each apparatus of the invention will require to be custom designed for the metal with which it is to be used and the range of particle sizes to be detected and, in particular, the range of currents that will be employed is relatively wide. Table I below gives the electrical resistivities of some typical metals to which the invention is applicable, the values being taken from the 8th Edition of "Metals Handbook", published by the American Society for Metals, 1964.

TABLE I

| METAL | TEMPERATURE °C. | ELECTRICAL RESISTIVITY $\mu\Omega$- m |
|---|---|---|
| Aluminum | 700 | 0.25 |
| Bismuth | 271 | 1.29 |
| Copper | 1083 | 0.22 |
| Iron (Steel) | 1536 | 1.39 |
| Gallium | 30 | 0.26 |
| Mercury | 100 | 1.03 |
| Sodium | 97 | 0.096 |
| Nickel | 1450 | 0.85 |
| Lead | 340 | 0.98 |
| Zinc | 413 | 0.35 |
| Magnesium | 650 | 0.27 |
| Potassium | 64 | 0.14 |
| Tin | 232 | 0.45 |
| Cadmium | 400 | 0.34 |

For example, if an aperture of 300 micrometers diameter is taken as standard then, as indicated above, the typical preferred current value for molten aluminium for the detection of particles in the range 20–150 micrometers is 60 amperes. If equivalent voltage pulses are to be obtained then molten sodium will require an applied current of about 150 amperes [$(60 \times 0.25) \div 0.096$], while molten iron will require an applied current of about 11.5 amperes [$(60 \times 0.25) \div 1.3$]. Again for example, with molten iron if the applied current is reduced to 1 ampere, while the lower limit for the detection of particles is 20 microvolts, then the smallest size of particle that can be readily detected rises from 20 micrometers to 45 micrometers [$20 \times (11.5)^{1/3}$]. With currently readily available equipment voltage pulses of less than 20 microvolts start to become indistinguishable from the background electrical noise. It will be seen therefore that the ultimate limits of particle sizes which can be detected depend upon the size of the aperture used, the metal to which the invention is applied, the current that is applied, and the threshold voltage pulses that can usefully be detected.

It has been found practical to provide the required constant current through the circuit from a current source comprising a 6 volt lead acid battery and an appropriate ballast resistor. It is desired to use a source that is as smooth and noise free in power delivery as possible and the D.C. battery system described is found to be effective and economical.

Figure 2:
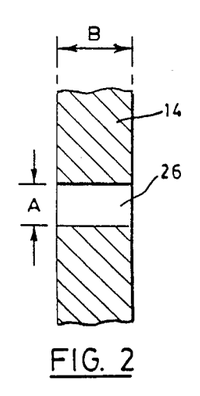
FIGS. 2, 3 and 4 are cross-sections to an enlarged scale through a sample-receiving vessel of the apparatus of FIG. 1 to show preferred forms of flow aperture.

The size and shape of the aperture is found to be unexpectedly critical in obtaining usable readings. A simple drilled opening as illustrated by FIG. 2 can be employed, but does have a tendency to cause turbulence in the flow through it. Thus, preferably it should not cause turbulence in the metal flow and to this end can be made of the shape of FIG. 4, in which it presents an opening to the entering molten metal that is considerably larger than its minimum cross-section area, and then tapers smoothly outwardly from the minimum area portion into the body of the test container. For detection of particles of about 20 micrometers effective diameter or larger suspended in aluminum the minimum area portion will need to have a diameter of less than 300 micrometers when using the preferred applied current of 60 amperes, the exact length of the passage being of no consequence. It can be shown that the signal amplitude is inversely proportional to the fourth power of the passage minimum diameter, but the sampling rate is dependent on flow rate through the passage and is therefore proportional to the passage cross-section area ($D^2$), and these two parameters are in conflict with one another. The problem of possible blockage of the passage by large particles of course increases with decrease of minimum diameter, and the values given are a practical compromise.

It can also be shown that there is a direct relationship between signal amplitude and current. A principal problem is the inevitable background noise and the usual precautions were taken to reduce this as far as possible, e.g. by twisting lead wires together, together with the unusual precaution particular to this invention of using a secondary battery as a D.C. power source. Background noise was also found to be caused by various other mechanical sources, such as vibration of the apparatus, and this must also be avoided as much as possible. In the specific example, the background noise was found to be about 5 microvolts RMS of which 2 microvolts was input noise of the amplifier. It is at present believed that one factor that permits operation of the method and apparatus is that the liquid metal surrounding the current passage serves as an excellent Faraday shield, which reduces the background noise to an acceptable value and permits the use of the necessary high-gain amplifiers.

Figure 3:
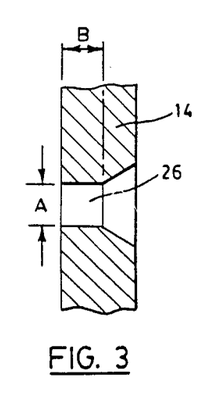

A passage of the form of FIG. 2 has a relatively long length of constant diameter; a long passage has the potential disadvantage that more than one particle can be passing through at any one time, but also has the potential advantage that the elongated pulse produced gives an opportunity of also examining the geometry of the particle. A passage of the cross-section illustrated by FIG. 3 is advantageous in reducing inflow turbulence and can be formed by drilling and countersinking, the resultant passage being of diameter A and effective length B; difficulty is experienced in counterboring the inner orifice because of the restricted space available. A preferred cross-section for the passage is illustrated by FIG. 4 in which the passage decreases smoothly, progressively and somewhat exponentially toward a central minimum, and increases in a corresponding manner away from the centre. It is found with a container of a glassy material that the orifice can readily be formed to this preferred profile by piercing with a suitably sized and shaped gas flame; the material softens and its surface energy moves it to form the preferred profile automatically. The sampling tube may be disposable.

It has also unexpectedly been found advantageous to precondition the newly-formed passage before a test is performed by passing an extremely heavy current (2 to 10 times the normal operating current) in the flow path for a specific minimum period of time. In the apparatus of FIG. 1 this can be obtained by closing the switch 33 and short-circuiting the ballast resistor 32. This preconditioning current will be in the range of 10 to 1000 amperes, and as a specific example, with an apparatus intended to operate with a normal test current of about 60 amps the preconditioning current should be in the range 120 to 600 amps. The preconditioning current will be applied for at least 1 to 5 seconds the period being increased if the lower currents are used. It is believed that this preconditioning may operate by causing intense local heating and possibly vaporization of the metal in the passage which attacks the surface and rids it of adsorbed gases and small holes, thus ensuring that the metal is in complete contact with the wall of the passage. This operation is also carried out if, during a test, it is observed that the baseline of the electrical recorder becomes unstable. In the latter case it is believed that the instability may be due to particles, particularly smaller particles, adhering to the passage wall, and that the intense localized heating by this preconditioning current increases the contact angle between the metal and any such particles, thus promoting their removal.

Owing to the high sensitivity required of the apparatus to obtain usable results above the level of the background noise present or generated during a test it was also found, as described above, that a completely quiescent vacuum source was necessary to draw the molten metal into the test container, since the pulses produced by any type of vacuum pump resulted in the imposition of an additional pulsing signal on the peak detector read-out that would otherwise have required computer analysis and filtering to remove. In the specific test equipment described above the vacuum reservoir used had a volume of about 10 liters, so that there was no substantial change of pressure during a test. The use of argon gas in the apparatus minimized any production of oxide particles that might subsequently cause errors if the sample is analysed by microscopic methods. The molten metal can alternatively be moved through the orifice by application of pressurized gas to the metal outside the container, but in practice this is not as satisfactory or as economical as the vacuum method described.

A specific form of the test apparatus employed as the differential amplifier 42 (type 5A22N of Tektronix) is the front end of a Tektronix type 5223 digitizing and storage oscilloscope that also served for direct observation of the signals. This differential amplifier is equipped with suitable selectable high and low pass filters. The maximum excursion of the particle pulses fed to the preamplifier was in the range of about 5–1000 microvolts on the 0.30 Volt baseline; for practical purposes the voltage difference was measured between the tips of the two current-carrying electodes 20 and 28, so that the D.C. component arises from the voltage drop along each electrode as well as the voltage drop across the path through the passage. Pulses smaller than 5 microvolts were completely lost in the overall background noise and the amplifier output was fixed at 50 millivolts per division; amplifier gains of 500–5000 were normally used by adjusting the sensitivity control. The log amplifier 44 and peak detector 46 consisted of a Tracor Northern type TN 1214 which gave a satisfactory output of about 0–10 volts and includes a sample and hold circuit capable of providing pulses of about 2 microseconds duration from the relatively long pulses of about 500 microseconds produced by the passages of the particles. These short pulses were required for the multichannel analyser 48 used, a Tracor Northern Model 1206, which has a ten bit analog/digital converter that will divide a 0–8 volt input into 510 equal voltage channels and count, store and display up to $10^6 - 1$ events per channel.

Figure 7:
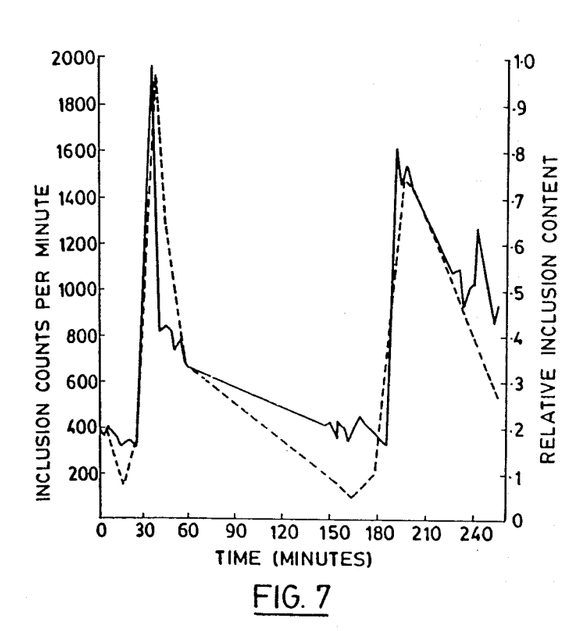
FIG. 7 shows a comparison of test results obtained employing an established porous disc filtration-metallographic enalysis technique (PoDFA system) with results obtained with experimental apparatus of the invention.

FIG. 6 shows a typical plot that is obtained with the method and apparatus of the invention as just specifically described. It will be noted that the graph begins at the channel equivalent to particles of size of equivalent spherical diameter about 20 micrometers and terminates at the channels equivalent to particles of size greater than about 50 micrometers, the number of particles detected decreasing progressively between these values. FIG. 7 will be referred to below.

In a method of operation according to the invention a sample of metal to be tested is provided from a stream or batch thereof and is tested by the method and using an apparatus of the invention. When the inclusion content for particulates of greater than the said predetermined value is above a given value as determined by operation of the invention then the stream or batch from which the sample was taken is treated to reduce the inclusion content, for example by directing the stream or batch to a suitable location at which the inclusion content is reduced for example by chlorine-nitrogen degassing or a repeat application of sparging gas.

Figure 8:
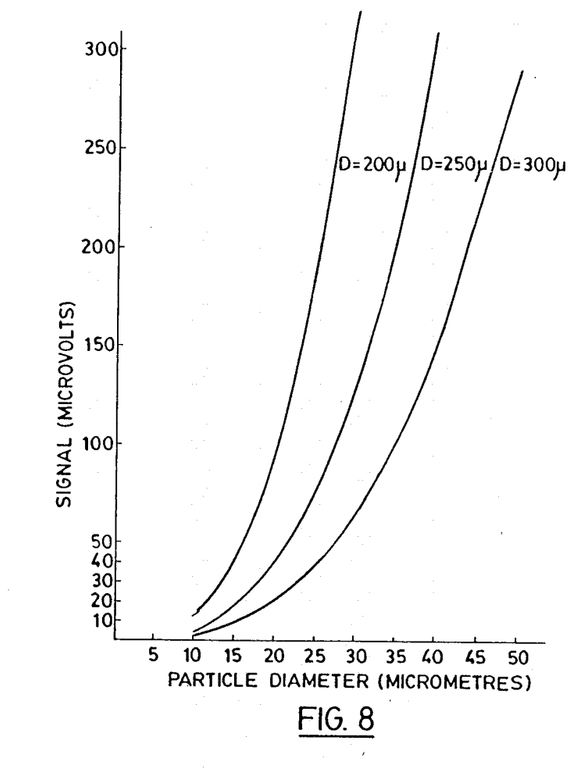
FIG. 8 shows the magnitude of voltage pulses obtained for particles of different sizes passing through apertures of different sizes using the apparatus of FIG. 1.

FIG. 8 shows in graphical form the magnitudes of the voltage pulses that will be observed when essentially non-conducting particles of various equivalent spherical diameters pass through holes of respectively 200, 250 and 300 μm diameter in the wall of the sample-receiving vessel. The equivalent particle diameter in micrometers is recorded on this graph abscissa, while the corresponding pulse magnitude in microvolts is recorded on the ordinate. These values given are for molten aluminium through which a test current of 60 amperes is passed, the value of $\rho$ being $25 \times 10^{-8}$ ohm-metres.

A series of examples are now provided to illustrate the use and versatility of the method and apparatus of the invention for the monitoring of molten metal cleanliness characteristics. Unless otherwise specified, the following set of operating conditions were used:

| | |
|---|---|
| Diameter of Passage (minimum) = | 300 micrometers |
| Electrical Current through Passage = | 60 amperes |
| Preamplifier Gain = | 1000 |
| Logarithmic amplifier response $V_{out}$(volts) = | $3.33 \log_{10} V_{in} + 6.67$ |
| Gauge Pressure during sampling = | −12.5 cm Hg (vacuum) |
| Minimum Particle Size Analysed for = (based on diameter of an equivalent volume sphere) | 20 micrometers |
| Liquid Metal Tested = | aluminum |

EXAMPLE 1

Instrument Calibration

Figure 9:
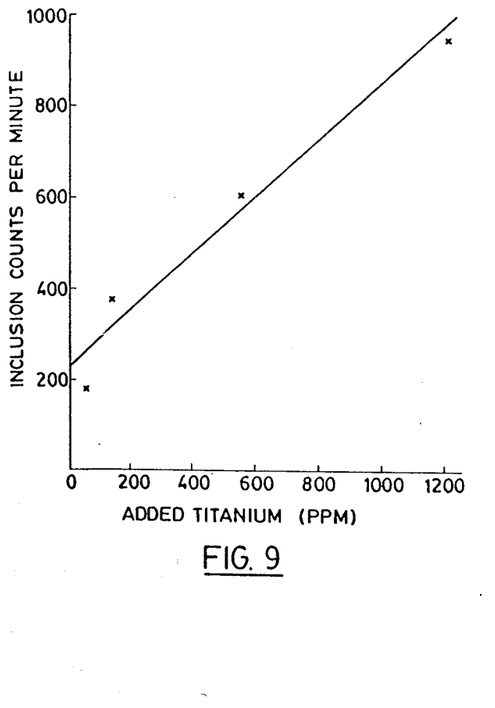
FIG. 9 is a graph of test results obtained from the deliberate addition to a bath of molten aluminum of known amounts of titanium diboride to provide less conductive inclusions.

A bath of 25 Kg of commercial purity aluminium was held within a temperature range of 710–725° C. and fed with a 9 mm diameter aluminum rod containing titanium diboride grain refining nuclei (Aluminium+5% Ti+1% B). Four successive additions were made to the stirred bath, resulting in the data points shown in FIG. 9. As expected, a linear correlation was obtained between the inclusion count rate (ordinate) and amount of titanium added (abscissa), the latter being computed in parts per million (PPM).

EXAMPLE 2

Titanium and Vanadium (Ti-V)B Precipitation from Aluminum Melts

This is an example of the use of the method and apparatus of the invention for studying the behaviour of inclusions in aluminum melts. Referring to Table 2 below, commercially pure aluminum was melted and held at 700° C. in a 100 Kg resistance heated furnace for a period of six hours (A). The melt was stirred (B), settled for two hours (C), and treated with a 20 p.p.m. addition of boron stirred into the melt (D) so as to nucleate and precipitate (Ti-V)B particles. Following subsequent periods of settling and stirring (E through I), a second boron addition of 85 p.p.m. was made (J), followed by final periods of settling and stirring (K-M).

Table 2 therefore gives a history of the melt's cleanliness as measured using the invention during the sequence of processing operations noted. It illustrates the settling characteristics of (Ti-V)B particles and demonstrates the requirement of minimal convection and stirring to rid aluminum melts of such impurity particles. It also illustrates the type of operation that can be achieved using the rapid test procedure provided by the invention.

EXAMPLE 3

Processing of Electrical Conductor Grade Aluminum

Following boron additions to a 50 tonne tilting furnace held at 710° C. for the precipitation of (Ti-V)B from the melt, tests were carried out to determine the influence of settling time on melt cleanliness. For this example samples of molten aluminum were taken from the transfer launder, into which metal from the tilting furnace was poured.

Figure 10:
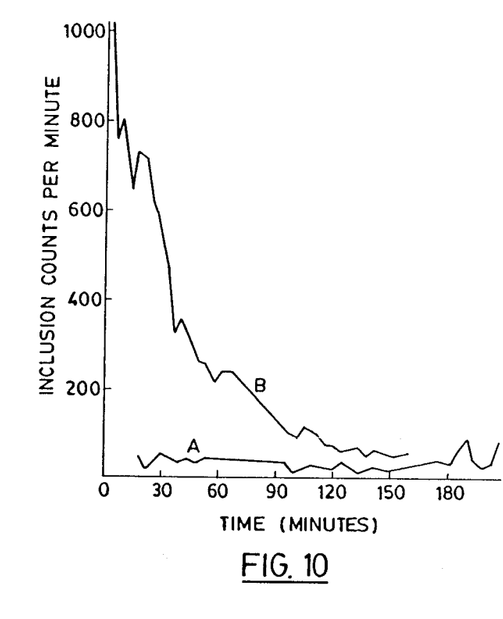
FIG. 10 shows a comparison between the cleanliness of poured aluminum using a standard practice (Curve A) requiring an initial settling period, and a different practice (Curve B) without an initial settling period.

FIG. 10 shows the results which it was possible to observe with the process and apparatus of the invention, namely the differences in melt cleanliness that were observed when standard operating practices for tilting furnaces were employed, as shown by curve A, in which an initial one hour settling period is observed, and when a different practice was employed (curve B); in which the tilting furnace was filled and emptying and casting procedures initiated immediately afterwards. Curve B shows the much higher inclusion count rate in excess of 1000 counts per minute (c.p.m.) obtained at the start of casting with this different practice, settling of (Ti-V)B particles within the tilting furnace subsequently resulting in cleaner exiting metal, with the entrained inclusions finally reaching more normal levels after 120 minutes of pouring to become similar to those registered by curve A.

EXAMPLE 4

Evaluation of Filter Bed Performance

A magnesium aluminum alloy was first treated by passing the melt prior to casting through a filter bed consisting of a box of tabular alumina balls, its purpose being to filter undesirable inclusions from the metal. The metal was sampled before and after the filter and the results are those given in Table 3 below, obtained after five minutes into casting. The Table shows the size distribution of particles before and after passage through the filter bed, and indicates the efficiency of the filter for different particle sizes.

The overall efficiency for particle removal was 70% and, as shown, appeared to be independent of equivalent particle diameter for sizes ranging between 16 and 50 micrometers. The apparent drop in efficiency at high particle diameters may be due, in part, to the random error in sampling procedure which increases in significance at the low count rates at larger particle sizes.

TABLE 2

| PROCESSING OPERATIONS | RESISTIVE PULSE READING (total counts per minute ≧ 20 μm) |
|---|---|
| A Metal held at 700° C. for 6 hrs. | 32 |
| B Melt stirred | 305 |
| C A 2 hr. settling period allowed | 108 |
| D a 20 p.p.m. addition of boron stirred into melt | 2750 |
| E Following a 5-minute settling period | 847 |
| F Melt stirred | 2767 |
| G Following a 5 minute settling period | 727 |
| H Following a 1 hr. settling period | 310 |
| I Following a further 1 hr., ten minute period | 295 |
| J An 85 p.p.m. addition of boron stirred into melt | 8405 |
| K Following a 10 minute settling period | 3527 |
| L Following an overnight (12 hr) settling period | 79 |
| M Melt stirred | 2748 |

TABLE 3

| Particle Size Micrometers | Counts Before Filter | Counts After Filter | Filter Efficiency |
|---|---|---|---|
| 16-20 | 740 | 210 | 72% |
| 20-25 | 460 | 115 | 75% |
| 25-30 | 158 | 47 | 70% |
| 30-34 | 69 | 19 | 72% |
| 35-40 | 38 | 12 | 68% |
| 40-45 | 14 | 9 | 36% |
| 45-50 | 8 | 5 | 38% |
| 50 | 14 | 13 | 7% |

EXAMPLE 5

Continuous Process Monitoring

Tests were carried out to monitor cleanliness levels during the casting of aluminum can stock from a tandem furnace continuous casting system. In this series of tests, the results were obtained employing the method and apparatus of the invention compared with those obtained with the known PoDFA system. In this latter test system (porous disc filtration apparatus) a sample of at least 1 Kg of molten aluminum is forced under pressure through a porous ceramic filter disc which will retain all solid inclusions of greater than a predetermined size. Some metal is allowed to remain on the disc and permitted to freeze. The disc and the sample are then sectioned and polished and the section examined microscopically by a trained observer. The procedure can only be regarded as semi-quantitative; there is some indication of particle size and size distribution and the composition and source of the inclusions can be deduced, but a highly skilled operator is needed and the time required to obtain useful test results is about 24-48 hours.

FIG. 7 therefore provides a comparison of the results obtained with the two cleanliness measurement techniques, those of the invention being shown in solid lines while those of the PoDFA technique are shown in broken lines. The results of the invention are recorded at the left ordinate in terms of inclusion count rate per minute, while those on the right ordinate scale are from the porous disc filtration analysis, in terms of the relative area of inclusions observed per unit sample weight. It will be seen that the results of the tests correlated relatively closely with one another, with the exception that the test results of the apparatus of the invention were immediately available in more detailed form. Table 4 below provides examples of the particle size distributions sampled at the 35, 55 and 150 minute mark respectively.

TABLE 4

| Particle Size Micrometers | Inclusions per Kg. after Elapsed Time | | |
|---|---|---|---|
| | 35 min | 55 min | 150 min |
| 20-25 | 22,350 | 12,000 | 6,300 |
| 25-30 | 10,800 | 2,700 | 1,350 |
| 30-35 | 5,400 | 1,500 | 600 |
| 35-40 | 3,150 | 600 | 300 |
| 40-45 | 1,800 | — | — |
| 45-50 | 1,800 | — | — |
| 50 | 1,800 | — | — |

The initial peak observed in FIG. 7 after 30 minutes corresponded to the completion of tapping from one furnace and the start of pouring from the second furnace. The large peak in particle count rate corresponded to the entrainment of surface impurities in the fresh stream of metal. Following the first 35 minutes of flow from that particular furnace, metal cleanliness improved as sedimentation of particles within the tandem furnace continued. After 185 minutes of casting, another furnace was tapped leading to another surge in entrained particulates, again followed by subsequent improvement in particle quality.

We claim:

1. A method for the detection and measurement in a molten metal sample of suspended particulates of greater than a predetermined size whose electrical conductivities differ from that of the suspending molten metal including the steps of:
   - establishing a current path which will include molten metal of the sample between two electrodes and through a passage of predetermined cross-sectional area,
   - passing the molten metal sample in the said current path and through the said passage while an electric current is maintained through the current path, and
   - measuring the voltage difference between the said electrodes and detecting changes therein caused by the passage through the passage of said particulates.

2. A method as claimed in claim 1, including the step of counting the number of said changes in voltage difference as a representation of the number of the said particulates in the sample, and measuring the size of the changes as representative of the sizes of the particulates causing the changes.

3. A method as claimed in claim 1, wherein the said passage is of effective cross-section minimum diameter from 100 to 5000 micrometers.

4. A method as claimed in claim 1, wherein the said passage is of effective cross-section minimum diameter from 200 to 500 micrometers.

5. A method as claimed in claim 1, wherein the current in the said current path at the passage is from 1 to 500 amperes.

6. A method as claimed in claim 1, wherein the said passage is of effective cross-section minimum diameter between 100 and 5000 micrometers, and the current in the said current path at the passage is from 1 to 500 amperes.

7. A method as claimed in claim 1, wherein the molten metal sample is passed through the passage under the effect of a vacuum derived from a quiescent vacuum source.

8. A method as claimed in claim 1, wherein the current in the said current path is from 1 to 500 amperes, and the said passage is conditioned by the passage through the path of a current of from 10 to 1000 amperes for a period of from 1 to 5 seconds.

9. A method of treating a molten metal for removal of non-metallic inclusions therefrom comprising the steps of:
   - (a) providing a sample of the molten metal from a stream or batch thereof,
   - (b) establishing a current path which will include molten metal of the sample between two electrodes and through a passage of predetermined cross-sectional area,
   - (c) passing the molten metal sample in the said current path and through the said passage while an electric current is maintained through the current path, and
   - (d) measuring the voltage difference between the said electrodes and detecting changes therein caused by the passage through the passage of said particulates.

(e) counting the number of said changes in voltage difference as a representation of the number of the said particulates in the sample, and measuring the size of the changes as representative of the sizes of the particulates causing the changes (f) when the inclusion content for particulates of greater than said predetermined value is above a given value treating the stream or batch of the metal to reduce the inclusion content thereof.

* * * * *